United States Patent
Politino et al.

(10) Patent No.: US 6,800,465 B2
(45) Date of Patent: Oct. 5, 2004

(54) **D-HYDANTOINASE FROM *OCHROBACTRUM ANTHROPI***

(75) Inventors: Michael Politino, Syracuse, NY (US); Sean M. Tonzi, Skaneateles, NY (US); Guna Romancik, Jamesville, NY (US); John J. Usher, Dewitt, NY (US); David A. Lowe, Fayetteville, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 95 days.

(21) Appl. No.: 10/114,810

(22) Filed: Apr. 3, 2002

(65) Prior Publication Data

US 2003/0013102 A1 Jan. 16, 2003

Related U.S. Application Data

(60) Provisional application No. 60/281,150, filed on Apr. 3, 2001.

(51) Int. Cl.[7] .......................... C12P 13/04; C12P 41/00; C12N 9/86; C12N 15/55
(52) U.S. Cl. .................... 435/106; 435/231; 435/320.1; 435/252.3; 435/280; 536/27.2
(58) Field of Search ............................ 435/231, 320.1, 435/252.3, 106, 280; 536/27.2

(56) References Cited

U.S. PATENT DOCUMENTS

| 5,516,660 A | 5/1996 | Wagner et al. .............. 435/106 |
| 5,714,355 A | 2/1998 | Wagner et al. .............. 435/106 |

FOREIGN PATENT DOCUMENTS

| EP | 0739978 A2 | 10/1998 |
| WO | WO9620275 | 4/1996 |
| WO | WO 00/58449 | 10/2000 |

OTHER PUBLICATIONS

DelVecchio, V.G., et al. (2002) Proc. Natl. Acad. Sci., USA 99(2), 443–448.*
Pozo, C., et al. (2002) J. Appl. Microbiol. 92, 1028–1034.*
NCBI Accession No. gi:14022051, Kaneko, et al., May 15, 2001.
NCBI Accession No. gi:23347063, Paulsen, et al., Sep. 30, 2002.
NCBI Accession No. gi:17983665, DelVecchio, et al., Mar. 20, 2003.
NCBI Accession No. gi:17987927, Paulsen, et al., Mar. 19, 2003.
NCBI Accession No. gi:13471607, Kaneko, et al., Dec. 9, 2002.
NCBI Accession No. gi:23347058, Paulsen, et al., Sep. 30, 2002.
NCBI Accession No. gi:17983663, DelVecchio, et al., Mar. 20, 2003.
NCBI Accession No. gi:17740858, Wood, et al., Dec. 20, 2001.
NCBI Accession No. gi:15157548, Hinkle, et al., Dec. 18, 2001.
NCBI Accession No. gi:3421364, Dai, et al., Aug. 18, 1998.
NCBI Accession No. gi:27355645, Kaneko, et al., Mar. 28, 2003.
NCBI Accession No. gi:15075230, Capela, et al., Jul. 5, 2002.
NCBI Accession No. gi:23501185, Paulsin, et al., Dec. 12, 2002.
Kaneko, et al. (2000) DNA Research 7:331–338.
Paulsen, et al. (2002) PNAS 99(20):13148–13153.
NCBI Accession No. gi:25290209, DelVecchio, et al., Apr. 19, 2002.
Capela, et al. (2001) PNAS 98(17):9877–9882.
Wood, et al. (2001) Science 294:2317–2323.

* cited by examiner

*Primary Examiner*—Charles L. Patterson, Jr.
(74) *Attorney, Agent, or Firm*—John A. Lamerdin

(57) ABSTRACT

The present invention relates to a novel D-hydantoinase from *Ochrobactrum anthropi* that enantio-selectively hydrolyzes D-hydantoins to their corresponding D-N-carbamoyl-amino acids; nucleic acids that encode for the enzyme; expression vectors including the nucleic acids; and host cells capable of expressing the enzyme.

22 Claims, 9 Drawing Sheets

5'- ALA, LYS, VAL, ILE, LYS, GLY                              SEQ ID NO:9

5'- GC(X), AA(GA), GT(X), AT(ACT), AA(GA),GG-3'              SEQ ID NO:8

Inverse:

5'- CC(TC),TT(AGT), AT(X), AC(TC), TT(X), GC-3'              SEQ ID NO:10

Probes:

1.   5'- CC(TC),TT(AGT), AT(C), AC(TC), TT(X), GC-3'         SEQ ID NO:4

2.   5'- CC(TC),TT(AGT), AT(T), AC(TC), TT(X), GC-3'         SEQ ID NO:5

3.   5'- CC(TC),TT(AGT), AT(A), AC(TC), TT(X), GC-3'         SEQ ID NO:6

4.   5'- CC(TC),TT(AGT), AT(G), AC(TC), TT(X), GC-3'         SEQ ID NO:7

FIG. 3

HYDANTOINASE

| Sequence | Position |
|---|---|
| GGGGCATTTCGACCCCGTGACATTCGACAATGGCTGCGTGGAGGCTATCCGCAATGCGGC | 60 |
| GGAACGGCTTGGCTACAGCCACCGCAATATCGTTTCGGGCGCAGGCCATGATGCCTGCTG | 120 |
| GGTCAATCGCGTGGCACCGACCGCCATGGTCATGTGCCCCTGCGTCGATGGCCTCAGCCA | 180 |
| TAACGAGGACGAGGACATTTCGAAAGAATGGGCGTCGGCGGGAACCGACGTGCTTCTGCA | 240 |
| TGCAGTATTGGAGACCGCTGAAATTGTGAGTTGATTTCGGGCTTCTCCGATACTGCTACT | 300 |
| GTTCGCAACAAAACCAAAAGGGGAACGACGAACAATGGCAAAGGTCATCAAAGGCGGAA | 360 |

```
                                          M  A  K  V  I  K  G  G  T
CCGTCATCACGGCTGACCGCACCTTTAAAGCCGATGTTCTCATCGAAGGCGAGAAGATCG    420
 V  I  T  A  D  R  T  F  K  A  D  V  L  I  E  G  E  K  I  V
TTGCCGTCGGCGACAATCTCTCCGGCGATGAAGTGATCGATGCATCCGGCTGCTATATCA    480
 A  V  G  D  N  L  S  G  D  E  V  I  D  A  S  G  C  Y  I  M
TGCCCGGCGGCATCGACCCGCACACCCATTTGCAGATGCCCTTCATGGGCACCTACTCCT    540
 P  G  G  I  D  P  H  T  H  L  Q  M  P  F  M  G  T  Y  S  S
CCGACGATTTCGATACCGGCACCGCCGCCGCGCTTGCGGGCGGCACCACGATGGTGGTCG    600
 D  D  F  D  T  G  T  A  A  A  L  A  G  G  T  T  M  V  V  D
ATTTCGTCCTGCCCGGCTCGGAGGGCAATCTTCTGGAAGCGTTGCAGGAATGGTTCCAGA    660
 F  V  L  P  G  S  E  G  N  L  L  E  A  L  Q  E  W  F  Q  K
AAGCGGGCAAGGCGCGCACCGACTATTCGTTCCACATGGCCATCACCGGCTGGAACGAGC    720
 A  G  K  A  R  T  D  Y  S  F  H  M  A  I  T  G  W  N  E  R
GAACCTTCAACGAAATGGCCGAAGTGGTGAAGCGCGGCATCAACACCTTCAAGCATTTCA    780
 T  F  N  E  M  A  E  V  V  K  R  G  I  N  T  F  K  H  F  M
TGGCCTACAAGGGCGCGCTGATGGTGAACGATGACGAGATGTTCGCTTCGTTCCAGCGCT    840
 A  Y  K  G  A  L  M  V  N  D  D  E  M  F  A  S  F  Q  R  C
GCGCGGAACTTGGCGCCATGCCGCTCGTCCATGCCGAAAACGGCGACATCGTCGCGCAAT    900
 A  E  L  G  A  M  P  L  V  H  A  E  N  G  D  I  V  A  Q  L
TGCAGGCGAAGCTGATGGCCGAAGGCAATGACGGGCCGGAAGCGCATGCCTATTCCCGCC    960
 Q  A  K  L  M  A  E  G  N  D  G  P  E  A  H  A  Y  S  R  P
CGCCCGAAGTCGAAGGCGAAGCCACCAACCGCGCCATCATGATTGCCGATCAGGCAGGCG   1020
 P  E  V  E  G  E  A  T  N  R  A  I  M  I  A  D  Q  A  G  V
TGCCGCTCTATGTCGTGCATGTCTCCTGCGAACAAAGCCATGAGGCGATCCGCCGTGCGC   1080
 P  L  Y  V  V  H  V  S  C  E  Q  S  H  E  A  I  R  R  A  R
GCCAGAAGGGAATGCGCGTTTTCGGCGAGCCCCTGATCCAGCATCTGACGCTCGATGAAA   1140
 Q  K  G  M  R  V  F  G  E  P  L  I  Q  H  L  T  L  D  E  S
```

FIG. 6A

```
GCGAATATCACAACCGGGACTGGGACTATGCGGCCCGTCGCGTCATGTCGCCGCCGTTCC    1200
  E  Y  H  N  R  D  W  D  Y  A  A  R  R  V  M  S  P  P  F  R

GTGACAAGGCCAATCAGGACAGTCTTTGGGCTGGCCTTGCGGCAGGAAGCCTGCAATGCG    1260
  D  K  A  N  Q  D  S  L  W  A  G  L  A  A  G  S  L  Q  C  V

TTGCGACTGACCATTGCGCTTTCACCACCGAGCAGAAGCGCTACGGCATCGGCAATTTCA    1320
  A  T  D  H  C  A  F  T  T  E  Q  K  R  Y  G  I  G  N  F  T

CCAAGATTCCAAACGGAACGGGTGGGCTGGAAGAACGCATGCCGGTGCTGTGGTCGCGCG    1380
  K  I  P  N  G  T  G  G  L  E  E  R  M  P  V  L  W  S  R  G

GCGTGCGCACCGGGCGCCTGACGCCAAACGAATTCGTGGCCGTTACCTCAACCAACATCG    1440
  V  R  T  G  R  L  T  P  N  E  F  V  A  V  T  S  T  N  I  A

CCAAGATATTGAACATCTATCCGCAGAAAGGCGCCGTTCTGCCGGGTGCGGATGCCGATC    1500
  K  I  L  N  I  Y  P  Q  K  G  A  V  L  P  G  A  D  A  D  L

TCGTCATCTGGGACCCGGAGGCCACCAGAAAGGTTTCCGCAAAGACCCAGCATTCCTCCA    1560
  V  I  W  D  P  E  A  T  R  K  V  S  A  K  T  Q  H  S  S  I

TCGATTACAACGTGTTCGAGGGCTTTGAACTCAAGGGCCTGCCGAAGATGACGCTTTCCC    1620
  D  Y  N  V  F  E  G  F  E  L  K  G  L  P  K  M  T  L  S  R

GCGGGCGGGTTGCTTTCGACAAGGGTAACGTCACGGCGGAACCCGGCGACGGACGCTTCA    1680
  G  R  V  A  F  D  K  G  N  V  T  A  E  P  G  D  G  R  F  I

TCGAGCGCGAGCCGAATGGCGCCGTCAATCGGGCGCTGTCGCAATGGAAGGAAATCGTTG    1740
  E  R  E  P  N  G  A  V  N  R  A  L  S  Q  W  K  E  I  V  A

CGCCGCGCAAGGTGGAGCGCAGCGCCGAACATATGCCGATAGGGGTCTGACACATGGCCAT    1800
  P  R  K  V  E  R  S  A  E  H  M  P  I  G  V  (SEQ ID NO:2)

CGTCCAGCTTCGGGAACCGCGCATGAGTTTGAATGACAGCATGGCCCCGAAGGGGCGAGG    1860

CAAATGCGCAGACCGTGATCGACATCAAGGACCTGTCGCTCGTCTTCGAGACGAATGACG    1920

GGCCGGTGCATGCGCTGTCGAATATCGATCTCGCCGTCAGGCCGGCGAGTTCGTTTCCTT    1980

CATCGGCCCTTCGGGATGCGGCAAGACAACGTTGATGCGTGTCGTCGCCGATCTCGAACG    2040

GCCTACCTCCGGCTCCGTCACCGTAAACGGGAAAACACCGGAACAAGCCCGCCTCGACCG    2100

GTCCTATGGTTA    (SEQ ID NO:1)                                    2113
```

SEQ ID NO:3 indicated by underlined bold type in above sequence.

FIG. 6B

SEQUENCE LISTING

<160> NUMBER OF SEQ ID NOS: 10

<210> SEQ ID NO 1
<211> LENGTH: 2113
<212> TYPE: DNA
<213> ORGANISM: Ochrobactrum anthropi

<400> SEQUENCE: 1

```
ggggcatttc gacccccgtga cattcgacaa tggctgcgtg gaggctatcc gcaatgcggc    60
ggaacggctt ggctacagcc accgcaatat cgtttcgggc gcaggccatg atgcctgctg   120
ggtcaatcgc gtggcaccga ccgccatggt catgtgcccc tgcgtcgatg gcctcagcca   180
taacgaggac gaggacattt cgaaagaatg gcgtcggcg ggaaccgacg tgcttctgca   240
tgcagtattg agaccgctg aaattgtgag ttgatttcgg gcttctccga tactgctact   300
gttcgcaaca aaaccaaaaa ggggaacgac gaacaatggc aaaggtcatc aaaggcggaa   360
ccgtcatcac ggctgaccgc acctttaaag ccgatgttct catcgaaggc gagaagatcg   420
ttgccgtcgg cgacaatctc tccggcgatg aagtgatcga tgcatccggc tgctatatca   480
tgcccggcgg catcgacccg cacacccatt gcagatgcc cttcatgggc acctactcct   540
ccgacgattt cgataccggc accgccgccg cgcttgcggg cggcaccacg atggtggtcg   600
atttcgtcct gcccggctcg gagggcaatc ttctggaagc gttgcaggaa tggttccaga   660
aagcgggcaa ggcgcgcacc gactattcgt tccacatggc catcaccggc tggaacgagc   720
gaaccttcaa cgaaatggcc gaagtggtga agcgcggcat caacaccttc aagcatttca   780
tggcctacaa gggcgcgctg atggtgaacg atgacgagat gttcgcttcg ttccagcgct   840
gcgcggaact tggcgccatg ccgctcgtcc atgccgaaaa cggcgacatc gtcgcgcaat   900
tgcaggcgaa gctgatggcc gaaggcaatg acgggccgga agcgcatgcc tattcccgcc   960
cgcccgaagt cgaaggcgaa gccaccaacc gcgccatcat gattgccgat caggcaggcg  1020
tgccgctcta tgtcgtgcat gtctcctgcg aacaaagcca tgaggcgatc cgccgtgcgc  1080
gccagaaggg aatgcgcgtt tcggcgagc ccctgatcca gcatctgacg ctcgatgaaa  1140
gcgaatatca caaccgggac tgggactatg cggcccgtcg cgtcatgtcg ccgccgttcc  1200
gtgacaaggc caatcaggac agtctttggg ctggccttgc ggcaggaagc ctgcaatgcg  1260
ttgcgactga ccattgcgct ttcaccaccg agcagaagcg ctacggcatc ggcaatttca  1320
ccaagattcc aaacggaacg ggtgggctgg aagaacgcat gccggtgctg tggtcgcgcg  1380
gcgtgcgcac cgggcgcctg acgccaaacg aattcgtggc cgttacctca accaacatcg  1440
ccaagatatt gaacatctat ccgcagaaag gcgccgttct gccgggtgcg gatgccgatc  1500
tcgtcatctg ggacccggag gccaccagaa aggtttccgc aaagacccag cattcctcca  1560
tcgattacaa cgtgttcgag ggctttgaac tcaaggcct gccgaagatg acgctttccc  1620
gcgggcgggt tgctttcgac aagggtaacg tcacggcgga acccggcgac ggacgcttca  1680
tcgagcgcga gccgaatggc gccgtcaatc gggcgctgtc gcaatggaag gaaatcgttg  1740
cgccgcgcaa ggtggagcgc agcgccgaac atatgccgat aggggtctga cacatggcca  1800
tcgtccagct tcgggaaccg cgcatgagtt tgaatgacag catggccccg aaggggcgag  1860
gcaaatgcgc agaccgtgat cgacatcaag gacctgtcgc tcgtcttcga gacgaatgac  1920
gggccggtgc atgcgctgtc gaatatcgat ctcgccgtca ggccggcgag ttcgtttcct  1980
tcatcggccc ttcgggatgc ggcaagacaa cgttgatgcg tgtcgtcgcc gatctcgaac  2040
```

```
ggcctacctc cggctccgtc accgtaaacg ggaaaacacc ggaacaagcc cgcctcgacc    2100
ggtcctatgg tta                                                       2113
```

<210> SEQ ID NO 2
<211> LENGTH: 484
<212> TYPE: PRT
<213> ORGANISM: Ochrobactrum anthropi

<400> SEQUENCE: 2

```
Met Ala Lys Val Ile Lys Gly Gly Thr Val Ile Thr Ala Asp Arg Thr
1               5                   10                  15

Phe Lys Ala Asp Val Leu Ile Glu Gly Glu Lys Ile Val Ala Val Gly
                20                  25                  30

Asp Asn Leu Ser Gly Asp Glu Val Ile Asp Ala Ser Gly Cys Tyr Ile
            35                  40                  45

Met Pro Gly Gly Ile Asp Pro His Thr His Leu Gln Met Pro Phe Met
        50                  55                  60

Gly Thr Tyr Ser Ser Asp Asp Phe Asp Thr Gly Thr Ala Ala Ala Leu
65                  70                  75                  80

Ala Gly Gly Thr Thr Met Val Val Asp Phe Val Leu Pro Gly Ser Glu
                85                  90                  95

Gly Asn Leu Leu Glu Ala Leu Gln Glu Trp Phe Gln Lys Ala Gly Lys
            100                 105                 110

Ala Arg Thr Asp Tyr Ser Phe His Met Ala Ile Thr Gly Trp Asn Glu
        115                 120                 125

Arg Thr Phe Asn Glu Met Ala Glu Val Val Lys Arg Gly Ile Asn Thr
    130                 135                 140

Phe Lys His Phe Met Ala Tyr Lys Gly Ala Leu Met Val Asn Asp Asp
145                 150                 155                 160

Glu Met Phe Ala Ser Phe Gln Arg Cys Ala Glu Leu Gly Ala Met Pro
                165                 170                 175

Leu Val His Ala Glu Asn Gly Asp Ile Val Ala Gln Leu Gln Ala Lys
            180                 185                 190

Leu Met Ala Glu Gly Asn Asp Gly Pro Glu Ala His Ala Tyr Ser Arg
        195                 200                 205

Pro Pro Glu Val Glu Gly Glu Ala Thr Asn Arg Ala Ile Met Ile Ala
    210                 215                 220

Asp Gln Ala Gly Val Pro Leu Tyr Val Val His Val Ser Cys Glu Gln
225                 230                 235                 240

Ser His Glu Ala Ile Arg Arg Ala Arg Gln Lys Gly Met Arg Val Phe
                245                 250                 255

Gly Glu Pro Leu Ile Gln His Leu Thr Leu Asp Glu Ser Glu Tyr His
            260                 265                 270

Asn Arg Asp Trp Asp Tyr Ala Ala Arg Arg Val Met Ser Pro Pro Phe
        275                 280                 285

Arg Asp Lys Ala Asn Gln Asp Ser Leu Trp Ala Gly Leu Ala Ala Gly
    290                 295                 300

Ser Leu Gln Cys Val Ala Thr Asp His Cys Ala Phe Thr Thr Glu Gln
305                 310                 315                 320

Lys Arg Tyr Gly Ile Gly Asn Phe Thr Lys Ile Pro Asn Gly Thr Gly
                325                 330                 335

Gly Leu Glu Glu Arg Met Pro Val Leu Trp Ser Arg Gly Val Arg Thr
            340                 345                 350
```

-continued

```
Gly Arg Leu Thr Pro Asn Glu Phe Val Ala Val Thr Ser Thr Asn Ile
        355                 360                 365

Ala Lys Ile Leu Asn Ile Tyr Pro Gln Lys Gly Ala Val Leu Pro Gly
    370                 375                 380

Ala Asp Ala Asp Leu Val Ile Trp Asp Pro Ala Thr Arg Lys Val
385                 390                 395                 400

Ser Ala Lys Thr Gln His Ser Ser Ile Asp Tyr Asn Val Phe Glu Gly
                405                 410                 415

Phe Glu Leu Lys Gly Leu Pro Lys Met Thr Leu Ser Arg Gly Arg Val
                420                 425                 430

Ala Phe Asp Lys Gly Asn Val Thr Ala Glu Pro Gly Asp Gly Arg Phe
            435                 440                 445

Ile Glu Arg Glu Pro Asn Gly Ala Val Asn Arg Ala Leu Ser Gln Trp
    450                 455                 460

Lys Glu Ile Val Ala Pro Arg Lys Val Glu Arg Ser Ala Glu His Met
465                 470                 475                 480

Pro Ile Gly Val
```

```
<210> SEQ ID NO 3
<211> LENGTH: 16
<212> TYPE: PRT
<213> ORGANISM: Ochrobactrum anthropi

<400> SEQUENCE: 3

Ala Lys Val Ile Lys Gly Gly Thr Val Ile Thr Ala Asp Arg Thr Phe
1               5                   10                  15

<210> SEQ ID NO 4
<211> LENGTH: 17
<212> TYPE: DNA
<213> ORGANISM: Ochrobactrum anthropi
<220> FEATURE:
<221> NAME/KEY: misc_feature
<222> LOCATION: (3)..(3)
<223> OTHER INFORMATION: wherein "n" can be "t" or "c"
<220> FEATURE:
<221> NAME/KEY: misc_feature
<222> LOCATION: (6)..(6)
<223> OTHER INFORMATION: wherein "n" can be "a", "g", or "t"
<220> FEATURE:
<221> NAME/KEY: misc_feature
<222> LOCATION: (12)..(12)
<223> OTHER INFORMATION: wherein "n" can be  "t" or "c"
<220> FEATURE:
<221> NAME/KEY: misc_feature
<222> LOCATION: (15)..(15)
<223> OTHER INFORMATION: wherein "n" can be "a", "g", "c", or "t"

<400> SEQUENCE: 4
ccnttnatca cnttngc                                                17

<210> SEQ ID NO 5
<211> LENGTH: 17
<212> TYPE: DNA
<213> ORGANISM: Ochrobactrum anthropi
<220> FEATURE:
<221> NAME/KEY: misc_feature
<222> LOCATION: (3)..(3)
<223> OTHER INFORMATION: wherein "n" can be " t" or "c"
<220> FEATURE:
<221> NAME/KEY: misc_feature
<222> LOCATION: (6)..(6)
<223> OTHER INFORMATION: wherein "n" can be "a", "g", or "t"
<220> FEATURE:
<221> NAME/KEY: misc_feature
<222> LOCATION: (12)..(12)
```

```
<223> OTHER INFORMATION: wherein "n" can be "t" or "c"
<220> FEATURE:
<221> NAME/KEY: misc_feature
<222> LOCATION: (15)..(15)
<223> OTHER INFORMATION: wherein "n" can be "a", "g", "t", or "c"

<400> SEQUENCE: 5
ccnttnatta cnttngc                                                    17

<210> SEQ ID NO 6
<211> LENGTH: 17
<212> TYPE: DNA
<213> ORGANISM: Ochrobactrum anthropi
<220> FEATURE:
<221> NAME/KEY: misc_feature
<222> LOCATION: (3)..(3)
<223> OTHER INFORMATION: wherein "n" can be "t" or "c"
<220> FEATURE:
<221> NAME/KEY: misc_feature
<222> LOCATION: (6)..(6)
<223> OTHER INFORMATION: wherein "n" can be "a", "g", or "t"
<220> FEATURE:
<221> NAME/KEY: misc_feature
<222> LOCATION: (12)..(12)
<223> OTHER INFORMATION: wherein "n" can be "t" or "c"
<220> FEATURE:
<221> NAME/KEY: misc_feature
<222> LOCATION: (15)..(15)
<223> OTHER INFORMATION: wherein "n" can be "a", "g", "t" or "c"

<400> SEQUENCE: 6
ccnttnataa cnttngc                                                    17

<210> SEQ ID NO 7
<211> LENGTH: 17
<212> TYPE: DNA
<213> ORGANISM: Ochrobactrum anthropi
<220> FEATURE:
<221> NAME/KEY: misc_feature
<222> LOCATION: (3)..(3)
<223> OTHER INFORMATION: wherein "n" can be "t"  or "c"
<220> FEATURE:
<221> NAME/KEY: misc_feature
<222> LOCATION: (6)..(6)
<223> OTHER INFORMATION: wherein "n" can be "a", "g",  or "t"
<220> FEATURE:
<221> NAME/KEY: misc_feature
<222> LOCATION: (12)..(12)
<223> OTHER INFORMATION: wherein "n" can be "t" or "c"
<220> FEATURE:
<221> NAME/KEY: misc_feature
<222> LOCATION: (15)..(15)
<223> OTHER INFORMATION: wherein "n" can be "a",  "g", "t", or "c"

<400> SEQUENCE: 7
ccnttnatga cnttngc                                                    17

<210> SEQ ID NO 8
<211> LENGTH: 17
<212> TYPE: DNA
<213> ORGANISM: Ochrobactrum anthropi
<220> FEATURE:
<221> NAME/KEY: misc_feature
<222> LOCATION: (3)..(3)
<223> OTHER INFORMATION: wherein "n" can be "a", "g", "t", or  "c"
<220> FEATURE:
<221> NAME/KEY: misc_feature
<222> LOCATION: (6)..(6)
<223> OTHER INFORMATION: wherein "n" can be "g" or "a"
<220> FEATURE:
<221> NAME/KEY: misc_feature
<222> LOCATION: (9)..(9)
<223> OTHER INFORMATION: wherein "n" can be "a",  "g", "t", or "c"
```

```
-continued

<220> FEATURE:
<221> NAME/KEY: misc_feature
<222> LOCATION: (12)..(12)
<223> OTHER INFORMATION: wherein "n" can be "a", "c", or "t"
<220> FEATURE:
<221> NAME/KEY: misc_feature
<222> LOCATION: (15)..(15)
<223> OTHER INFORMATION: wherein "n" can be "g" or "a"

<400> SEQUENCE: 8
gcnaangtna tnaangg                                                17

<210> SEQ ID NO 9
<211> LENGTH: 6
<212> TYPE: PRT
<213> ORGANISM: Ochrobactrum anthropi

<400> SEQUENCE: 9

Ala Lys Val Ile Lys Gly
1               5

<210> SEQ ID NO 10
<211> LENGTH: 17
<212> TYPE: DNA
<213> ORGANISM: Ochrobactrum anthropi
<220> FEATURE:
<221> NAME/KEY: misc_feature
<222> LOCATION: (3)..(3)
<223> OTHER INFORMATION: wherein "n" can be "t" or "c"
<220> FEATURE:
<221> NAME/KEY: misc_feature
<222> LOCATION: (6)..(6)
<223> OTHER INFORMATION: wherein "n" can be "a", "g", or "t"
<220> FEATURE:
<221> NAME/KEY: misc_feature
<222> LOCATION: (9)..(9)
<223> OTHER INFORMATION: wherein "n" can be "a", "g", or "t", or "c"
<220> FEATURE:
<221> NAME/KEY: misc_feature
<222> LOCATION: (12)..(12)
<223> OTHER INFORMATION: wherein "n" can be  "t" or "c"
<220> FEATURE:
<221> NAME/KEY: misc_feature
<222> LOCATION: (15)..(15)
<223> OTHER INFORMATION: wherein "n" can be "a", "g",  "t", or "c"

<400> SEQUENCE: 10
ccnttnatna cnttngc                                                17
```

D-HYDANTOINASE FROM OCHROBACTRUM ANTHROPI

CROSS-REFERENCE TO RELATED APPLICATIONS

This application claims the benefit of U.S. Provisional Application No. 60/281,150, filed Apr. 3, 2001, the contents of which are herein incorporated by reference in their entirety.

FIELD OF THE INVENTION

The present invention relates to a novel D-hydantoinase from *Ochrobactrum anthropi* that enantio-selectively hydrolyzes D-hydantoins to their corresponding D-N-carbamoyl-α-amino acid; the nucleic acid that encodes for the enzyme; an expression vector including the nucleic acid; and a host cell capable of expressing the enzyme.

BACKGROUND OF THE INVENTION

Hydantoinase is an enzyme that catalyzes the conversion of 5-monosubstituted hydantoins to the corresponding N-carbamoyl-α-amino acids. The optically pure N-carbamoyl-α-amino acids can then be hydrolyzed by chemical or enzymatic means to amino acids. This important entantioselective property makes them valuable for the production of optically pure D- or L-amino acids, which are useful intermediates for the preparation of semisynthetic penicillins and cephalosporins. The use of hydantoinase to produce optically pure N-carbamoyl amino acids is known in the art [Syldatk, C., Muller, R., Siemann, M., Krohn, K., and Wagner, F. (1992). In Biocatalytic production of amino acids and derivatives. (D. Rozell and F. Wagner, Ed.) p.75–128 Hanser Publishers, New York]. Hydantoinase enzymes have been isolated from a variety of sources including Klebsiella, Corynebacterium, Agrobacterium, Pseudomonas, Bacillus, and Streptomyces. European Patent Application EP/0739978 A2 describes a hydantoinase produced from Agrobacterium tumefaciens exhibiting improved activity and stability in alkaline medium at high temperatures. U.S. Pat. No. 5,516,660 discloses novel specimens of the Arthrobacter species which produce hydantoinases that are capable of producing L-α-amino acids from D-, L- and/or D,L-5-monosubstituted hydantoins. U.S. Pat. No. 5,714,355 describes a mutant specimen of the Arthrobacter species which has up to 2.7 fold greater enzymatic activity than the parent organism. PCT Publication WO 00/58449 describes modified hydantoinases that exhibit improved enzymatic properties relative to previously isolated hydantoinases. There still remains a need to isolate new enzymes that exhibit improved enantioselectivity as well as catalytic activity.

SUMMARY OF THE INVENTION

The present invention is directed to isolated and purified D-hydantionase from *Ochrobactrum anthropi* preferably having the sequence of SEQ ID NO: 2 or a protein having at least 80% identity to SEQ ID NO: 2.

The present invention is also directed to nucleic acids coding for the enzyme, preferably the genomic DNA of SEQ ID NO: 1 or cDNA derived therefrom.

The present invention is also directed to a recombinant host cell comprising nucleic acid coding for the enzyme of the invention.

The present invention is also directed to an expression vector comprising nucleic acid coding for the enzyme of the invention.

Further, the present invention is directed to a method for producing the enzyme of the invention comprising culturing a suitable cell containing nucleic acid coding for the enzyme of the invention in a suitable medium under conditions suitable for expression of the enzyme.

Finally, the present invention is directed to a process for converting 5-monosubstituted hydantoins to the corresponding N-carbamoyl-α-amino acids using the hydantoinase of the invention to result in a product of high chiral purity.

BRIEF DESCRIPTION OF THE DRAWINGS

FIG. 3: Fragments of DNA and polypeptide useful in the present invention. Probes 1–4 were used to obtain the enzyme of the invention. Probes 1 through 4 are, respectively, SEQ ID NOS: 4 through 7. The amino acid sequence is SEQ ID NO: 9, which is encoded by the DNA sequence immediately below the amino acid sequence (SEQ ID NO: 8). The inverse of SEQ ID NO:8 is SEQ ID NO:10.

FIG. 6: Genomic DNA sequence encoding the enzyme of the invention (SEQ ID NO:1) and the amino acid sequence of the enzyme of the invention (SEQ ID NO:2). N-terminal sequence (SEQ ID NO:3) determined by Edman sequencing is shown in underlined boldface type.

DETAILED DESCRIPTION OF THE INVENTION

Figure 1:
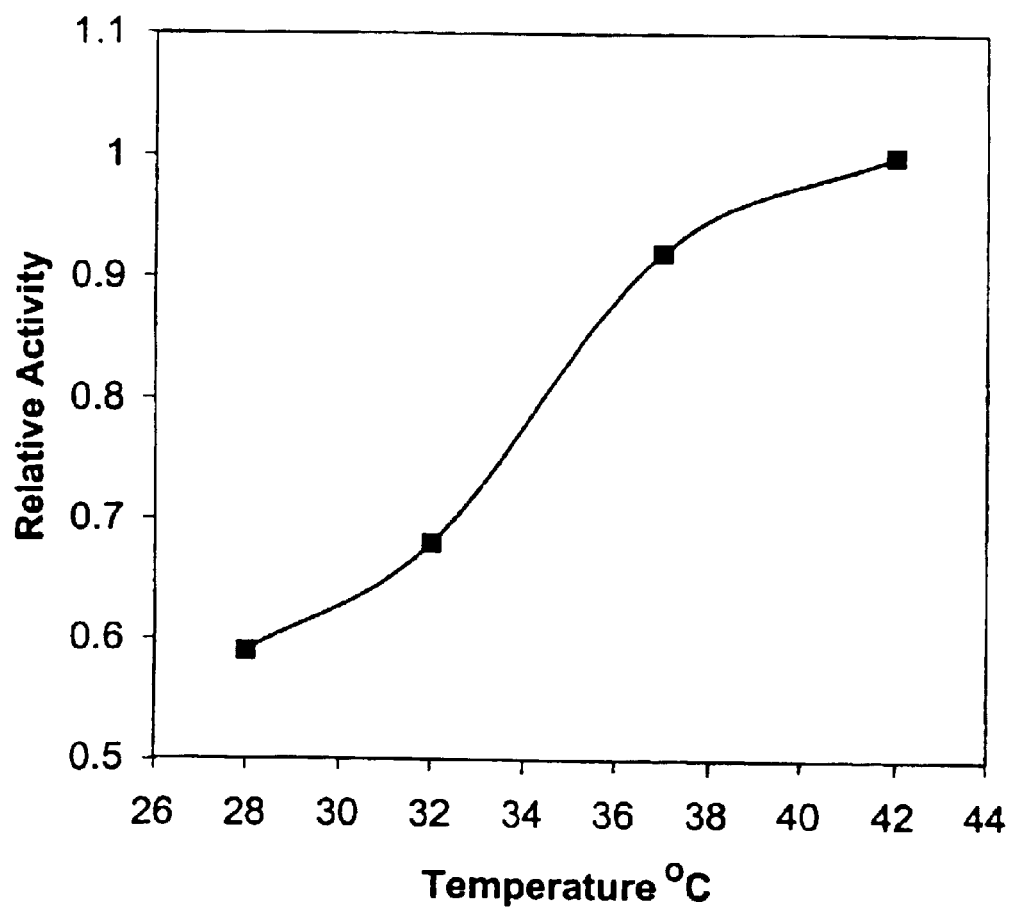
FIG. 1: Temperature profile of hydantoinase activity in whole cells.

The present invention relates to an isolated nucleic acid molecule comprising a nucleic acid sequence coding for all or part of hydantoinase from *Ochrobactrum anthropi*. A preferred strain of *Ochrobactrum anthropi* is ATCC 202035, deposited with the American Type Culture Collection, Rockville, Md., U.S.A., under the provisions of the Budapest Treaty. Preferably, the nucleic acid molecule is a DNA molecule and the nucleic acid sequence is a DNA sequence. All DNA sequences are represented herein by formulas whose left to right orientation is in the conventional direction of 5' to 3'. Nucleotide base abbreviations used herein are conventional in the art, i.e., T is thymine, A is adenine, C is cytosine, and G is guanine; also, X is A,T,C, or G, Pu is purine (i.e., G or A), and Py is pyrimidine (i.e., T or G). Further preferred is a DNA sequence having all or part of the nucleotide sequence substantially as shown in FIG. 6 (SEQ ID NO:1), or a DNA sequence complementary to this DNA sequence; or a DNA sequence which hybridizes to SEQ ID NO:1 or its component. Preferably, the DNA sequence hybridizes under stringent conditions. Stringent hybridization conditions select for DNA sequences of greater than 80% homology, preferably greater than 85% or, more preferably, greater than 90% homology. Screening DNA under stringent conditions can be carried out according to the method described in *Nature*, 313: 402–404 (1985), the contents of which are herein incorporated by reference. The DNA sequences capable of hybridizing under stringent conditions with the DNA disclosed in the present application may be, for example, allelic variants of the disclosed DNA sequences, may be naturally present in *Ochrobactrum anthropi*, but related to the disclosed DNA sequence, or may be derived from other bacterial sources. General techniques of nucleic acid hybridization are disclosed by Maniatis, T. et al., In: *Molecular Cloning, a Laboratory Manual*, Cold Spring Harbor, N.Y. (1982), and by Haymes, B. D. et al., In: *Nucleic Acid Hybridization, a Practical Approach*, IRL Press, Washington, D.C. (1985), which references are incorporated herein by reference. In the case of a nucleotide sequence (i.e., a DNA sequence) coding for part of the hydantoinase, it is preferred that the nucleotide sequence be at least about 15 nucleotides in length.

Preferred DNA fragments are the probes of SEQ ID NOS:4–7 (probes numbers 1–4, respectively in FIG. 3).

The hydantoinase molecules of the present invention do not necessarily need to be catalytically active. For example, catalytically inactive enzyme or fragments thereof may be useful in raising antibodies to the protein.

It is also contemplated that the present invention encompasses modified or variant sequences. As used in the present application, the term "modified" or "variant", when referring to a nucleotide or polypeptide sequence, means a nucleotide or polypeptide sequence which differs from the wild-type sequences specifically disclosed herein.

The DNA sequences of the present invention can be obtained using various methods well known to those of ordinary skill in the art. At least three alternative principal methods may be employed:

(1) the isolation of a double-stranded DNA sequence from genomic DNA or complementary DNA (cDNA) which contains the sequence;
(2) the chemical synthesis of the DNA sequence; and
(3) the synthesis of the DNA sequence by polymerase chain reaction (PCR).

In the first approach, a genomic or cDNA library can be screened in order to identify a DNA sequence coding for all or part of the hydantoinase. For example, an *O. anthropi* genomic DNA library can be screened in order to identify the DNA sequence coding for all or part of the enzyme. Various techniques can be used to screen the genomic DNA or cDNA libraries.

For example, labeled single stranded DNA probe sequences duplicating a sequence present in the target genomic DNA or cDNA coding for all or part of the enzyme can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of the hydantoinase using immunoblotting techniques.

In one typical screening method suitable for either immunoblotting or hybridization techniques, the genomic DNA library, which is usually contained in a vector, or cDNA library is first spread out on agar plates, and then the clones are transferred to filter membranes, for example, nitrocellulose membranes. A DNA probe can then be hybridized or an antibody can then be bound to the clones to identify those clones containing the genomic DNA or cDNA coding for all or part of the hydantoinase.

In the second approach, the DNA sequences of the present invention coding for all or part of the hydantoinase can be chemically synthesized. For example, the DNA sequence coding for the hydantoinase can be synthesized as a series of 100 base oligonucleotides that can be sequentially ligated (via appropriate terminal restriction sites or complementary terminal sequences) so as to form the correct linear sequence of nucleotides.

In the third approach, the DNA sequences of the present invention coding for all or part of the hydantoinase can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White et al., Trends Genet. 5, 185–189 (1989).

The DNA sequences of the present invention can be used in a variety of ways in accordance with the present invention. The most apparent use of the DNA sequence is to prepare hydantoinase to be useful for the conversion of 5-monosubstituted hydantoins to the corresponding N-carbamoyl-a-amino acids. However, they also can be used as DNA probes to screen other cDNA and genomic DNA libraries as to select by hybridization other DNA sequences that code for proteins related to hydantoinase. In addition, the DNA sequences of the present invention coding for all or part of the hydantoinase can be used as DNA probes to screen other cDNA and genomic DNA libraries to select, by hybridization, DNA sequences that code for hydantoinase molecules from organisms other than *O. anthropi*.

The DNA sequences of the present invention coding for all or part of the hydantoinase can also be modified (i.e., mutated) to prepare various mutations. Such mutations can be either degenerate, i.e., the mutation changes the amino acid sequence encoded by the mutated codon, or non-degenerate, i.e., the mutation does not change the amino acid sequence encoded by the mutated codon. These modified DNA sequences can be prepared, for example, by mutating the hydantoinase DNA sequence so that the mutation results in the deletion, substitution, insertion, inversion or addition of one or more amino acids in the encoded polypeptide using various methods known in the art. For example, the methods of site-directed mutagenesis described in Morinaga et al., Bio/Technol. 2, 636–639 (1984), Taylor et al., Nucl. Acids Res. 13, 8749–8764 (1985) and Kunkel, Proc. Natl. Acad. Sci. USA 82, 482–492 (1985) may be employed. In addition, kits for site-directed mutagenesis can be purchased from commercial vendors. For example, a kit for performing site-directed mutagenesis can be purchased from Amersham Corp. (Arlington Heights, Ill.). In addition, disruption, deletion and truncation methods as described in Sayers et al., Nucl. Acids Res. 16, 791–802 (1988) may also be employed. Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the present invention.

The present invention further concerns expression vectors comprising a DNA sequence coding for all or part of the hydantoinase of the invention. The expression vectors preferably contain all or part of one of the DNA sequences having the nucleotide sequences substantially as shown in FIG. 6. Further preferred are expression vectors comprising one or more regulatory DNA sequences operatively linked to the DNA sequence coding for all or part of the hydantoinase. As used in this context, the term "operatively linked" means that the regulatory DNA sequences are capable of directing the replication and/or the expression of the DNA sequence coding for all or part of the hydantoinase.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front (i.e., upstream of) the DNA sequence and followed by the DNA sequence coding for all or part of the hydantoinase structural protein. The DNA sequence coding for all or part of the structural protein is followed by transcription termination sequences and the remaining vector. The expression vectors can also include other DNA sequences known in the art, for example, stability leader sequences which provide for stability of the expression product, secretory leader sequences which provide for secretion of the expression product, sequences which allow expression of the structural gene to modulated (i.e., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. For example, when cloning in a fungal cell system, the expression vector should contain promoters isolated from the genome of fungal cells (i.e., the trpC promoter from *Aspergillus nidulans*). Certain expression vectors may contain a fungal autonomously replicating sequence (ARS; i.e., ARS from *Fusarium oxysporum* and *Saccharomyces cerevisiae*) which promotes in vivo production of self-replicating plasmids in fungal hosts. It is preferred that the fungal expression vectors of the invention do not have a fungal ARS sequence and thus will integrate into host chromosomes upon plasmid entry of host cells. Such integration is preferred because of enhanced genetic stability. An expression vector as contemplated by the present invention is at least capable of directing the replication in *Escherichia coli* and integration in fungal cells, and preferably the expression, of the hydantoinase DNA sequence of the present invention. Suitable origins of replication in *E. coli* various hosts include, for example, a ColEI plasmid replication origin. Suitable promoters include, for example, the trpC promoter from *A. nidulans* and the neo-r gene promoter from *E. coli*. Suitable termination sequences include, for example, the trp C terminator from *A. nidulans*, and the neo-r gene terminator from *E. coli*. It is also preferred that the expression vector include a sequence coding for a selectable marker. The selectable marker is preferably antibiotic resistance. As selectable markers, phleomycin resistance (for fungal cells), ampicillin resistance, and neomycin resistance (for bacterial cells) can be conveniently employed. All of these materials are known in the art and are commercially available.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The present invention additionally concerns host cells containing an expression vector that comprises a DNA sequence coding for all or part of hydantoinase. The host cells preferably contain an expression vector, which comprises all or part of one of the DNA sequence having the nucleotide sequences substantially as shown in FIG. 6.

Further preferred are host cells containing an expression vector comprising one or more regulatory DNA sequences capable of directing the replication and/or the expression of and operatively linked to a DNA sequence coding for all or part of the hydantoinase. Additionally included are host cells containing an expression vector which comprises a DNA sequence which has been modified (i.e., disrupted, deleted or truncated) so as to code for a hydantoinase molecule which is not catalytically active. Suitable host cells include both eukaryotic and prokaryotic host cells, for example, *E. coli* cells. Suitable eukaryotic host cells include, for example, *R. toruloides, Cephalosporium acremonium*, and *Penicillium chrysogenum* cells. A preferred host cell is *E. coli* ATCC 98563 containing plasmid pBMS2000, deposited with the American Type Culture Collection, Rockville, Md., U.S.A., under the provisions of the Budapest Treaty.

Expression vectors may be introduced into host cells by various methods known in the art. For example, transfection of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of large amounts of the hydantoinase.

Host cells containing an expression vector which contains a DNA sequence coding for all or part of the hydantoinase may be identified by one or more of the following five general approaches: (a) DNA-DNA hybridization; (b) the presence or absence of marker gene functions; (c) assessing the level of transcription as measured by the production of hydantoinase mRNA transcripts in the host cell; (d) detection of the gene product immunologically; and (e) enzyme assay, enzyme assay being the preferred method of identification.

In the first approach, the presence of a DNA sequence coding for all or part of the hydantoinase can be detected by DNA-DNA or RNA-DNA hybridization using probes complementary to the DNA sequence.

In the second approach, the recombinant expression vector host system can be identified and selected based upon the presence or absence of certain marker gene functions (i.e., acetamide utilization, resistance to antibiotics, resistance to fungicide, uracil prototrophy, etc.). A marker gene can be placed in the same plasmid as the DNA sequence coding for all or part of the hydantoinase under the regulation of the same or a different promoter used to regulate the hydantoinase coding sequence. Expression of the marker gene in response to induction or selection indicates the presence of the entire recombinant expression vector that carries the DNA sequence coding for all or part of the hydantoinase.

In the third approach, the production of hydantoinase mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of the hydantoinase can be assessed immunologically, for example, by Western blotting.

In the fifth approach, expression of hydantoinase can be measured by assaying for the hydantoinase enzyme activity using known methods.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns polypeptide molecules comprising all or part of the hydantoinase, said polypeptide molecules preferably having all or part of the amino acid sequence substantially as shown in FIG. 6. In the case of polypeptide molecules comprising part of hydantoinase, it is preferred that polypeptide molecules be at least about 10 amino acids in length.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

| SYMBOL | | |
|---|---|---|
| 1-letter code | 3-letter code | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described in Houghton et al., Proc. Natl. Acad. Sci. 82, 5131–5135 (1985) may be employed. It is preferred that the polypeptides be obtained by production in prokaryotic or eukaryotic host cells expressing a DNA sequence coding for all or part of the hydantoinase, or by in vitro translation of the mRNA encoded by a DNA sequence coding for all or part of the hydantoinase. For example, the DNA sequence of FIG. 6 may be synthesized using PCR as described above and inserted into a suitable expression vector, which in turn may be used to transform a suitable host cell. The recombinant host cell may then be cultured to produce the hydantoinase. Techniques for the production of polypeptides by these means are known in the art, and are described herein.

The isolated and purified D-hydantoinase of the invention preferably has the sequence of SEQ ID NO:2 or a protein having at least 80% homology to SEQ ID NO:2.

The variant amino acid or DNA sequences within the scope of the invention are homologous to the sequences specifically disclosed herein. The degree of homology (percent identity) between a specifically disclosed and a variant sequence may be determined, for example, by comparing the two sequences using the GAP computer programs, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl Math* 2:482, 1981). Briefly, the GAP program defines similarity as the number of aligned symbols (i.e., nucleotides or amino acids) which are similar, divided by the total number of symbols in the shorter of the two sequences. The preferred. default parameters for the GAP program include: (1) an unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

The polypeptides produced in this manner may then be isolated and purified using various protein purification techniques. For example, chromatographic procedures such as ion exchange chromatography, gel filtration chromatography and immunoaffinity chromatography may be employed.

As used herein, the term "isolated and purified" means the D-hydantoinase is substantially free of the constituents present in a natural or cellular environment.

In addition to the conversion process of the invention, the polypeptides of the present invention may be used in a variety of other ways. For example, the polypeptides can be used to prepare in a known manner polyclonal or monoclonal antibodies capable of binding the polypeptides. These antibodies may in turn be used for the detection of the polypeptides of the present invention in a sample, for example, a cell sample, using immunoassay techniques, such as radioimmunoassay or enzyme immunoassay. The antibodies can also be used in affinity chromatography for purifying the polypeptides of the present invention and isolating them from various sources.

Due to the degeneracy nature of the genetic code, which results from there being more than one codon for most of the amino acid residues and stop signals, other DNA sequences which encode the same amino acid sequence as depicted in FIG. 6 may be used for the production of the polypeptides of the present invention. In addition, it will be understood that allelic variations of these DNA and amino acid sequences naturally exist, or may be intentionally introduced using methods known in the art. These variations can be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphatic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The present invention further concerns a method for producing hydantoinase comprising culturing a host cell containing an expression vector capable of expressing the hydantoinase of the invention ("bioproduction" process).

The hydantoinase of the invention is an enzyme that stereoselectively catalyzes the conversion of 5-monosubstituted hydantoins to the corresponding D-N-carbamoyl—amino acids, and therefore the invention is additionally directed to this process ("conversion" process). The conversion process of the invention is steroselective,i.e., producing primarily the D-isomer even when the starting material is a racemic mixture of D and L-isomers. The conversion process can utilize pure hydantoinase, partially purified or crude hydantoinase, or whole cells.

The conversion process of the invention can be depicted as follows:

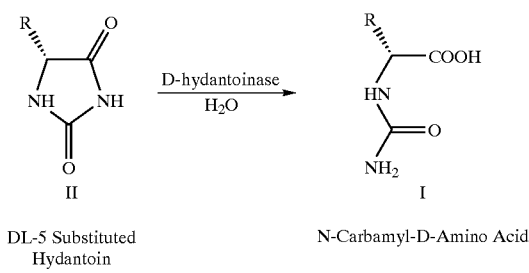

DL-5 Substituted Hydantoin    N-Carbamyl-D-Amino Acid wherein R is H or a hydrocarbon moiety. The specific chemical nature of the "R" moiety is not important since the D-hydantoinase enzyme of the invention specifically acts on the hydantoin moiety.

The N-carbamyl-D-amino acid produced by the above reaction is optionally converted in a second step to a D-amino acid as depicted below.

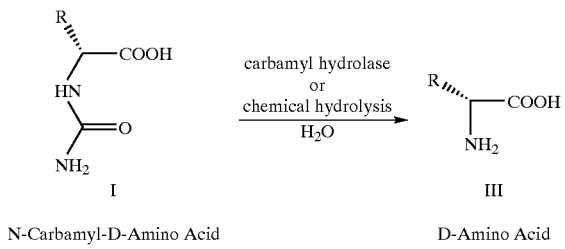

N-Carbamyl-D-Amino Acid    D-Amino Acid wherein R is as defined herein above.

The above second step can be accomplished via chemical or enzymatic methods using conventional procedures known in the art, such as the HONO method of Bayer (Takehahashi, et al., *J. Fermentation Technology*, 57:328, 1979).

The conversion process of the present invention may be carried out subsequent to the fermentation of the host cell employed (two-stage fermentation and conversion), or concurrently therewith, that is, in the latter case, by in situ fermentation and conversion (single-stage fermentation and conversion). In the single-stage process, the microorganisms can be grown in an appropriate medium until sufficient growth of the microorganisms is attained. A compound of Formula II can then be added to the microbial cultures and the stereoselective enzymatic conversion continued with the fermentation, preferably until complete conversion is obtained.

In the two-stage process, the microorganisms can, in the first stage, be grown in an appropriate medium for fermentation until exhibiting the desired enzymatic activity. Subsequently, the cells can be harvested by centrifugation, and microbial cell suspensions prepared by suspending harvested cells in an appropriate buffered solution. Buffers such as tris-HCl, phosphates, sodium acetate and the like may be used. Water can also be used to prepare suspensions of microbial cells. In the second stage, the compound of Formula II can be mixed with the microbial cell suspensions, and the stereoselective enzymatic conversion catalyzed by the microbial cell suspension. The conversion is preferably conducted until all or nearly all, of the compound of Formula II is stereoselectively hydrolyzed.

In the conversion process, the cells can be immobilized by conventional procedures known in the art (see, for example, *Immobilized Enzymes for Industrial* Reactors, 1975, Ed. R. Messing, Academic Press, New York; and *Immobilized Microbial Cells ACS Symposium Series* 106, 1979, K. Venkasubramanian, American Chemical Society, Washington D.C.). Immobilization can involve the covalent attachment or entrapment of cells or hydantoinase extracts or can involve the adsorption of cells to inorganic or organic surfaces. The hydantoinase extract or appropriately induced whole cells can be immobilized by covalent attachment onto various support matrices such as agarose, cellulose, dextran, glass, HYPOL (Hampshire Chemicals, Lexington, Mass.), polyacrylamide co-polymers or polystyrene or by entrapment with alginate, carrageenan, agar, polyacrylamide or microencapsulated within polymer membranes such as cellulose nitrate/acetate, nylon, lipid polyamide and the like or by adsorption to inorganic or organic surfaces such as silica, alumina, kaolin, ion exchange resins, porous glass, clay, cellulose, collagen, calcium phosphate gel, bentonite, carbon or Type Z and Type CZ biocarriers (W.R. Grace & Company). After the conversion is complete, the immobilized enzyme can be physically separated from the reaction mixture and used for subsequent reactions.

Growth of the microorganisms for either bioproduction of the enzyme or for in situ enzymatic conversion can be achieved by one of ordinary skill in the art by the use of an appropriate medium. Appropriate media for growing microorganisms include those that provide nutrients necessary for the growth of the microbial cells, and can vary substantially depending upon the growth requirements of the particular host cell. A typical medium for growth includes necessary carbon sources, nitrogen sources, and trace elements. Inducers can also be added. The term "inducer", as used herein, includes any compound enhancing formation of the desired enzymatic conversion activity within the microbial cell. Suitable inducers include hydantoin, hydantoinic acid and Formula I compounds. The amount of inducer is typically about 0.1 to about 1.0 weight percent of total reaction mixture.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; and alcohols such as ethanol, propanol and the like. Nitrogen sources can include N-Z amine A, corn steep liquor, soy bean meal, beef extracts, yeast extracts, molasses, baker's yeast, tryptone, nutrisoy, peptone, yeastamine, sodium nitrate, ammonium sulfate and the like.

Trace elements can include phosphates and magnesium, manganese, calcium, cobalt, nickel, iron, sodium and potassium salts.

The medium employed can include more than one carbon or nitrogen source or other nutrient.

Preferred media include aqueous media containing the following (in weight %):

| Medium 1 | Medium 2 |
|---|---|
| Malt Extract 1% | Peptone 0.3% |
| Yeast Extract 1% | Glycerol 4% |
| Peptone 1% | Malt Extract 1% |
| Glucose 2% | Yeast Extract 1% |
| pH 7.0 | pH 7.0 |

The pH of the medium is preferably adjusted to about 6 to 8, most preferably 6.5, sterilized, i.e., at a temperature of 121° C. for 30 minutes, and then adjusted to a pH of about 6.5 to 7.5, preferably 7.0, after sterilization.

During growth of host cells, the pH of the medium is preferably maintained between 4.0 and 9.0, most preferably between 6.0 and 8.0. For the conversion process using pre-formed hydantionase, the pH is preferably between about 8 and 11, more preferably between about 9 and 10.

Temperature is a measure of the heat energy available for the bioproduction and conversion processes and should be maintained to ensure that there is sufficient energy available for this process. A suitable temperature range for the processes of the invention involving growth of host cells is from about 15° C. to about 60° C. A preferred temperature range is from about 25° C. to about 40° C. If pre-formed hydantoinase is used for the conversion process, the temperature is preferably between about 30° C. to about 75° C., more preferably between about 40° C. about 45° C.

Pressure is not known to be critical to practice of the invention and for convenience, atmospheric pressure is typically employed.

The processes of the invention utilizing growing host cells are preferably carried out under aerobic conditions. The agitation and aeration of the reaction mixture affects the amount of oxygen available during the stereoselective reduction process which can be conducted, for example, in shake-flask cultures or fermentor tanks during growth of microorganisms in a single-stage or two-stage process. An agitation range from 50 to 500 RPM is preferable, with 50 to 100 RPM being most preferred. Aeration of about 0.1 to 10 volumes of air per volume of media per minute (i.e., 0.1 to 10 v/v) is preferred, with aeration of about 5 volumes of air per volume of media per minute (i.e., 5 v/VT) being most preferred.

In the stereoselective conversion process, complete conversion of the compound of Formula II may take, for example, from about 4 to 48 hours, preferably 12 to 24 hours, measured from the time of initially treating the compound of Formula II with a microorganism (i.e., host cell) or enzyme as described herein. The formation of the reaction product can be monitored by high performance liquid chromatography (HPLC) or by simple calorimetric assays.

It is preferred to employ an aqueous liquid as the reaction medium for the conversion process, although an organic liquid, or a miscible or immiscible (biphasic) organic/aqueous liquid mixture may also be employed when using pre-formed hydantoinase.

In the conversion process, it is preferred to employ 0.1 to 30 weight % of the compound of Formula II starting material based on the combined weight of the compound and reaction medium. High concentrations of hydantoins can be suspended in solvents such as methanol to about 10% (wt.) concentration to increase their solubility. The amount of enzyme or microorganism employed relative to the starting material is selected to allow catalysis of the stereoselective enzymatic conversion of the present invention.

In the conversion process using preformed enzyme, hydantoinase is generally added to a concentration of about 0.5 to about 10 units per ml.

The products of the stereoselective conversion process of the present invention may be isolated and purified by known methodologies such as by extraction distillation, crystallization, column chromatography, and the like.

A preferred method for separating the desired compound of Formula I from the remaining compounds of the reaction medium is by passing the reaction mixture through an Amicon (Beverly, Mass.) S10Y3 spiral ultrafiltration cartridge or similar product. The deproteinated permeate containing the N-carbamyl D-amino acids can be cleaved to the respective D-amino acid by conventional chemical technology. The retentate containing the hydantoinase can be used for a subsequent conversion process.

The conversion process of the present invention results in high yield of the compound of Formula I. A typical yield is greater than about 80%, preferably greater than about 90%, more preferably greater than about 95%, and most preferably about 99%. The present process also results in excellent optical purity. Typical optical purity is greater than about 90%, preferably greater than about 95% and most preferably greater than 99%.

The following examples are further illustrative of the present invention. These examples provide further understanding of the invention, and are not intended to limit the scope of the present invention.

EXAMPLES

Example 1

Use of Whole Cells of *Ochrobactrum anthropi* as Hydantoinase Enzyme Source 1.1 Consecutive Conversion Runs with Washed Cells of *Ochrobactrum anthropi*

*Ochrobactrum anthropi* was inoculated, a loopful from trypticase soy (pH 8.0) slant into two flasks of 100 ml BPYNH production medium per 500 ml regular flask, and shaken at 37° C. for 24 hours.

BPYNH Production Medium:

| 0.5% | Beef Extract Powder |
|---|---|
| 0.5% | Yeast Extract |
| 1% | Bacto-Peptone |
| 0.15% | NaCl |
| 0.1% | hydantoin |

(pH 8.0)

Whole broths (200 ml) were centrifuged 12,000 rpm at 10° C. 15 minutes, washed once with 0.9% saline, resuspended in 10 ml saline in 125 ml flasks and prewarmed to 37° C. DL-p-hydroxyphenyl hydantoin (200 mg aliquots) was suspended in 5 ml 400 mM TAPS buffer pH 8.7 and prewarmed to 37° C. Cell suspensions were added, pH quickly adjusted to 8.5 with 1N NaOH, final volume adjusted to 20 ml with $H_2O$, and incubations shaken in stoppered flasks at 37° C. Samples were taken (800 μl) and inactivated with 200 μl 12% TCA. Supernatants were assayed as previously described. Percent conversion results are summarized in the following table.

TABLE 1

Reuse of washed cells, % conversion:

| 1st use | | 2nd use | | 3rd use | |
|---|---|---|---|---|---|
| 1 hour | 5 hrs | 24 hrs | 4.5 hrs | 23 hrs | 5 hrs | 23 hrs |
| 5% | 18% | 54% | 9% | 34% | 12% | 27% |

1.2 Temperature Profile of Hydantoinase Activity

Culture was inoculated into BPYNH production medium 100 ml per 500 ml regular flask and shaken at 37° C. for 22 hours. Washed cells, 1 ml were incubated at 10×concentration in 0.45% saline/100 mM TAPS pH 8.5/10 mg per ml DL-p-hydroxyphenyl hydantoin at 28°, 32°, 37°, and 42° C. for 5 hours and 24 hours. Reactions were terminated with 250 μl 12% TCA and supernatants assayed. Relative activities appear in FIG. 1. Optimal activity occurs at temperatures greater than 42° C.

1.3 Effect of Glutaraldehyde and Acetone Treatment of Whole Cells

Washed cell suspension 0.5 ml aliquots of culture was treated with 0.5 ml glutaraldehyde (G.A.) final concentration 2% in phosphate buffer pH 7.0, or with 0.5 ml G.A. 2% in phosphate buffer and 1 ml acetone, or with 0.5 ml acetone alone at room temperature for 10 minutes. The treated cells were washed with 10 ml 0.9% saline and then with saline +1 mg/ml ammonium sulfate and resuspended in 1 ml 100 mM TAPS buffer pH 8.5. Resuspended cell suspensions were incubated with 10 mg/ml D,L-p-hydroxyphenyl hydantoin in 100 mM TAPS pH 8.5 (final volume 800 μl) at 42° C. for 4 hours. Reactions were terminated with 200 μl TCA 12% and assayed.

TABLE 2

Effect of glutaraldehyde and acetone on hydantoinase activity:

| Treatment | Relative Activity |
|---|---|
| Control (buffer only) | 1 |
| Glutaraldehyde | 1.2 |
| Glutaraldehyde/Acetone | 1.2 |
| Acetone | 2.8 |

1.4 pH Optimum of Hydantoinase Activity

Figure 2:
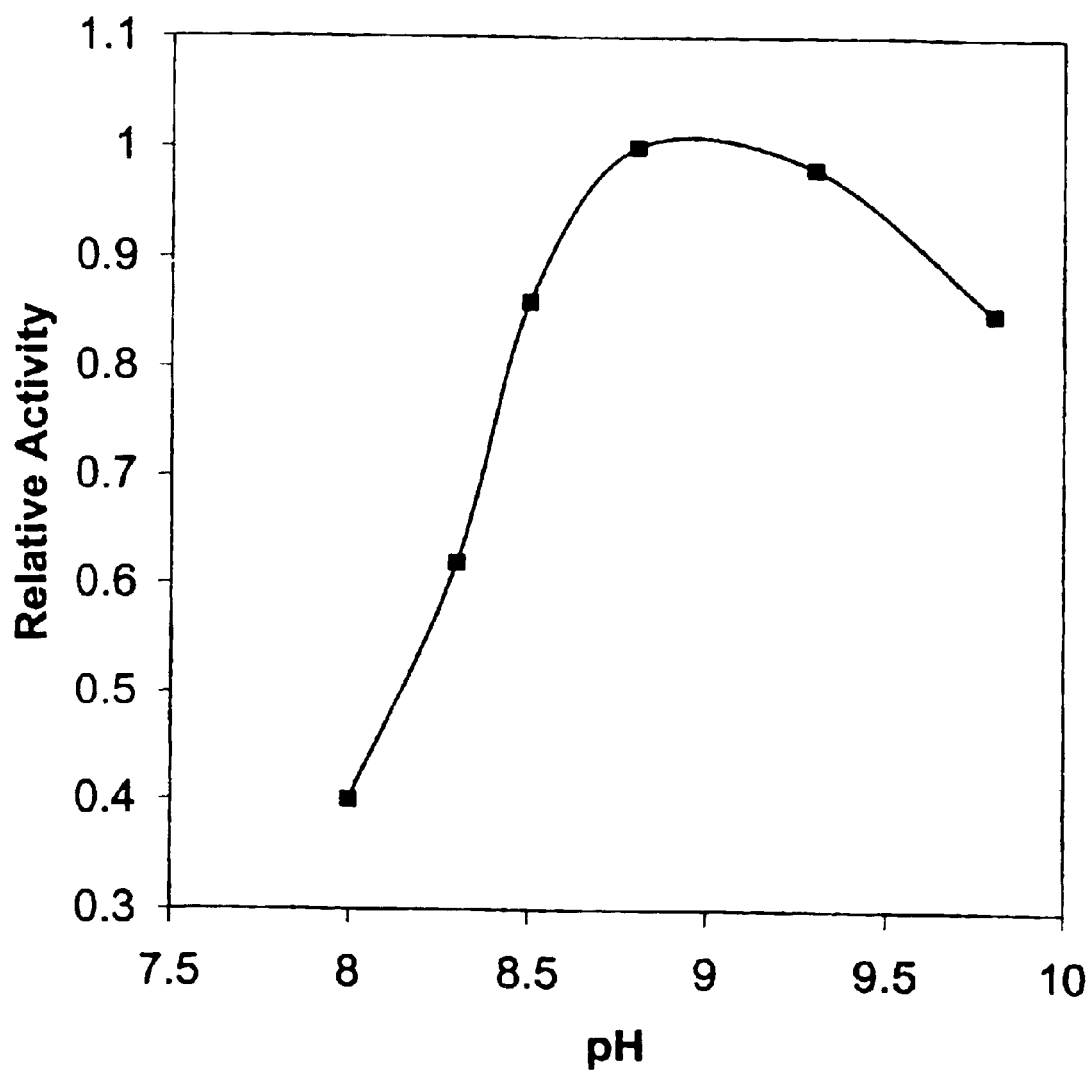
FIG. 2: pH optimum of hydantoinase activity in glutaraldehyde-treated cells.

Using a glutaraldehyde treated cell concentrate of *Ochrobactrum anthropi*, incubations were done with 10 mg/ml DL-p-hydroxyphenyl hydantoin in 200 mM TAPS buffer at various pHs and 42° C. pH range 8.0–8.8 was covered in one experiment and pH 8.8–9.8 in another run. pH adjustments back to normal were made at sampling times and at least every 30 minutes. FIG. 2 shows the optimum pH of activity at pH 8.8.

1.5 Stability of Enzyme at pH 8.8, 9.3 and 9.8

Glutaraldehyde treated cells from pH profile study were held at pH 8.8, 9.3 and 9.8 for about 4 hours. Solids were washed, resuspended in 25 mM TAPS pH 8.8 and 10 mg/ml D,L-p-hydroxyphenyl hydantoin and incubated at 42° C. for 4 hours. Results showed greatest stability of enzyme at pH 8.8 treatment. Optimum pH of activity at 8.8 in pH profile study was probably due to greater enzyme stability at pH 8.8 rather than pH 9.3 or 9.8.

TABLE 3

Stability of hydantoinase at alkaline pH:

| pH | Relative Activities |
|---|---|
| 8.8 | 1.75 |
| 9.3 | 1.17 |
| 9.8 | 0.62 |

1.6 Effect of Substrate Concentration on Rate of Conversion

The D,L-p-hydroxyphenyl hydantoin substrate is not completely soluble at 5 mg/ml and so suspensions were made and incubated with glutaraldehyde treated cells. Incubations were in 200 mM TAPS pH 8.8, 42° C. for 6 hours, and pH adjustments were made back to normal at least every hour. Reaction was assayed and product formed in mg/ml is recorded below.

TABLE 4

Effect of Substrate Concentration on Rate of Conversion

| Substrate mg/ml Conversion | 30 min | 60 min | 2¾ hr | 4 hr | 6 hr | % |
|---|---|---|---|---|---|---|
| 5 | .56 | 1.0 | 1.9 | 2.1 | 2.2 | 40% |
| 10 | .75 | 1.4 | 3.4 | 4.0 | 4.4 | 40% |
| 20 | .82 | 1.5 | 4.0 | 6.2 | 7.7 | 35% |
| 50 | .95 | 1.6 | 4.2 | 6.3 | 9.2 | 17% |

1.7 Immobilization of Hydantoinase

Crude extract of hydantoinase was obtained by microfluidizing of washed cell concentrate. Enzyme was immobilized on celite by slurrying crude extract and celite with two volumes of acetone and 4% glutaraldehyde and washed with water. Solids were recovered by centrifugation and had an activity of about 0.3 IU per gram of damp weight.

After reaction with immobilized enzyme, the reaction mixture was filtered to remove enzyme, then evaporated to one tenth volume. The pH was adjusted to 5.0, the mixture treated with activated charcoal and the filtrate adjusted to pH 2.0. The N-carbamoyl amino acid crystallized immediately, and after storage at 0° C. for 1 hour, the crystals were filtered and washed with water and dried.

The optical rotation of this material was measured and compared with the value for authentic D-N-carbamoyl (4-hydroxyphenyl glycine) prepared in this laboratory and with the literature value.

TABLE 5

Optical rotation of enzymatically generated product
[α]20D (C = 0.5%, 50:50 aqueous ethanol)

| Enzymatic D-N-Carbamoyl Amino Acid | −170.80° |
|---|---|
| Synthetic D-N-Carbamoyl Amino Acid | −173.08° |
| Literature Rotation | −175° |

This rotation clearly shows that the material isolated from the bioreactor has the D-configuration. It also shows that it is at least 98% pure.

1.8 Reuse of Immobilized Hydantoinase

Glutaraldehyde immobilized enzyme (9.23 grams damp weight) was suspended in 20 ml 400 mM TAPS pH 8.7, 400 mg D,L-p-hydroxyphenyl hydantoin added, overlaid with nitrogen and shaken at 42° C., 130 rpm for 23 hours. Initially pH dropped for up to 4 hours or so, but eventually stabilized and even rose slightly. pH was adjusted back to normal about once every hour for the first six hours and 800 µl sampled, inactivated with 200 µl 12% TCA and assayed. At 24 hours enzyme solids were washed with water, fresh substrate added, and returned to incubate as before for three consecutive runs. Enzyme was stored in H₂O between runs 2 and 3.

Results in terms of mg/ml of carbamoyl amino acid appear in the following table. (Runs 2 and 3 reflect a carryover of approximately 1–1.3 mg/ml of product).

TABLE 6

Reuse of Immobilized Hydantoinase (mg/ml product)

| Hour | Day 1/Run 1 | Day 2/Run 2 | Day 3/Run 3 |
|------|-------------|-------------|-------------|
| 1    | 1.8         | 2.8         | 2.3         |
| 2    | 2.8         | —           | 3.1         |
| 3    | —           | 7.1         | —           |
| 4    | 5.9         | —           | 5.7         |
| 5    | —           | 10.2        | —           |
| 6    | 9.2         | —           | 7.8         |
| 7    | 10.4        | —           | 9.4         |
| 22   | —           | 10.9        | —           |
| 23   | 10.9        | —           | —           |

Final Recovery of Hydantoin:

| Day 1       | Day 2       | Day 3       |
|-------------|-------------|-------------|
| 273 mg (62%) | 255 mg (58%) | 274 mg (63%) |

Example 2

Purification and Characterization of Hydantoinase from *Ochrobactrum anthropi*

2.1 Purification of Hydantoinase

Slant cultures on trypticase soy 3% or YNH agar (pH 8.0) were inoculated into 100 ml YNH medium per 500 ml regular flasks and shaken 250 rpm at 28° C. for 24 hours. Seed was crossed at 4% into 100 ml CSH-8 medium (pH 7.0) per 500 ml regular flask and shaken 250 rpm at 28° C. for 24 hours. (Final whole broth pH~7.9–8.1)

| YNH: 1% yeast extract powder | CSH-8: 8% corn steep liquor |
|------------------------------|------------------------------|
| 0.15% NaCl                   | 0.5% sucrose                 |
| 0.1% hydantoin               | 0.1% hydantoin               |
| (pH 8.0)                     | (pH 7.0)                     |

Whole cells were harvested from 10 liter broth by centrifugation and resuspended to 1.0 liter in H₂O. The cells were disrupted by passing 3 times through microfluidizer (Microfluidics Corporation). The mixture was centrifuged to remove cell debris and the resulting pellet was washed once with 200 ml. The final volume of crude enzyme obtained was 1.3 liter.

Ammonium sulfate to 60% of saturation was added to the clarified fraction. The precipitated enzyme was collected by centrifugation. The pellet was dissolved in 50 mM HEPES pH 7.5 to a final volume of 250 ml. The enzyme was centrifuged to remove remaining inactive solids. The enzyme was dialyzed overnight against 50 mM HEPES pH 7.5 buffer and concentrated in a Centriprep 30 (30,000 MWCO) to 50 ml.

The concentrated enzyme solution was applied to a 45×300 mm DEAE Trisacryl column pre-equilibrated with 50 mM HEPES pH 7.5. The column was washed again with 2-column volumes of the same buffer. The enzyme was eluted with a gradient of 0–300 mM NaCl over 500 ml in 50 mM HEPES pH 7.5. Fractions were assayed for protein content and activity. The peak active fractions were concentrated in a Centriprep 30 (30,000 MWCO) to approximately 2.0 ml.

Concentrate from DEAE Trisacryl column was applied to a 10×300 mm Superose 12 column (pre-equilibrated with 50 mM HEPES pH 7.5) and eluted with about 60 ml of the same buffer.

The peak active fractions for the Superose 12 column were pooled and concentrated to 1.0 ml on a Centricon 30 (30,000 MWCO) and applied to a 1 mm 10% polyacrylamide gel and run under native conditions. The gel was sliced into sections and the individual sections were assayed for activity. The sections containing the hydantoinase activity were electroeluted to recover enzyme. The enzyme obtained by this process was >90% homogeneous as determined by SDS-Page.

2.2 Molecular Weight Determination of Hydantoinase

Gel filtration chromatography indicated the molecular weight of the native hydantoinase to be approximately 100,000 to 110,000 Daltons.

Heat denatured samples of hydantoinase run on reducing SDS gel gave a single band at approximately 53,000 Daltons, while on non-reducing SDS gel the same sample gave nearly equal intensity bands at 57,000 and 53,000 Daltons indicating that the hydantoinase protein is probably a homodimer (53,000) with a secondary structure running at 57,000.

Unboiled samples of enzyme on non-reducing SDS gel gave a single band at about 100,000 Daltons confirming the results obtained by gel filtration chromatography.

2.3 Specific Activity of Hydantoinase

Active band eluant from preparative native gel was assayed and protein determined by Pierce Microtiter assay protocol using BSA standard. Specific activity was determined at greater than 4 IU per mg of protein.

2.4 PI Value of Hydantoinase

Active band eluant from preparative native gel was run on the Phast System IEF-PAGE gel with a pH range of 3–9 using low MW protein markers and the gel was silver stained. PI of active band protein was determined at approximately 4.5.

2.5 N-Terminal Amino Acid Sequence of Hydantoinase

The N-terminus of the 53,000 Da subunit was determined by automated Edman sequencing to be: Ala-Lys-Val-Ile-Lys-Gly-Gly-Thr-Val-Ile-Thr-Ala-Asp-Arg-Thr-Phe (SEQ ID NO:3)

Example 3

Isolation of the Gene Encoding Hydantoinase from *Ochrobactrum anthropi*

3.1 Preparation of Chromosomal DNA from *Ochrobactrum anthropi*.

Two 125 ml flasks containing 25 ml of seed media were inoculated from a slant of *Ochrobactrum anthropi*. The cultures were grown at 28° C., 250 rpm for 24 hours in 1.5% yeast extract, 0.15% NaCl, 0.1% hydantoin, pH 8.0. Cells were harvested by centrifugation, lysed, and digested in TE (10 mM Tris-Cl pH 8.0, 1 mM EDTA) buffer containing 100 µg/ml proteinase K and 0.5% SDS. The suspension was incubated at 37° C. for 1 hour. The mix was then precipitated in 10% CTAB (hexadecyltrimethylammonium bromide, Sigma H-5882) in 0.7 M NaCl at 65° C. for 20 minutes to remove cell wall debris, polysaccharides, and remaining proteins. (Wilson, K. (1994) Preparation of Genomic DNA from Bacteria, in F. M. Ausubel, R. Brent, R. E. Kingston, D. D. Moore, J. A. Smith, J. G. Seidman, and K. Struhl (Eds.), Current Protocols in Molecular Biology. John Wiley & Sons, New York.) The mixture was extracted twice, first with chloroform: isoamyl alcohol (24:1), then with phenol:chloroform:isoamyl alcohol (25:24:1) and precipitated in isopropanol. The DNA pellet was dissolved in TE containing 100 µg/ml RNase A and incubated at 22° C. for 16 hours. A second proteinase K/SDS digestion was performed and the organic extractions and ethanol precipitation were repeated. The DNA was dissolved in TE. The DNA concentration was determined spectrophotometrically at 260 nm.

3.2 Construction of Genomic DNA Library of *Ochrobactrum anthropi*

From the N-terminal amino acid sequence (experimental section 2.5 above) four 17-mer degenerate oligonucleotide probes were synthesized with the Applied Biosystems 391 DNA Synthesizer PCR-MATE (FIG. 3), end-labeled with $\gamma[^{32}P]ATP$ (Amersham AH 9968), and used to probe a Southern blot (see Southern, E. M. 1975, J. Mol. Biol. 98:503–517) of *O. anthropi* chromosomal DNA digested with restriction endonucleases BamHI, EcoRI, and HindIII. Hybridization was conducted in TMAC solution (3 M TMAC, 0.1 M Na₃PO4, pH 6.8, 5× Denhardt's, 1% SDS, 100 µg/ml denatured salmon sperm DNA, 1 mM EDTA) buffer at 46° C. for 18 hours. TMAC is tetramethylammoniumchloride, Sigma T-3411. Southern blots of the HindIII digest of the chromosomal DNA identified two fragments 6 Kb and 12 Kb, which hybridized to one of the N-terminal oligonucleotide probes. *O.anthropi* chromosomal DNA was digested with HindIII, electrophoresed through a 0.8% SeaPlaque (FMC) preparative agarose gel in TAE (0.04 M Tris-acetate, 0.002 M EDTA) buffer at 10 volts for 16 hours. Gel slices containing 5–7 Kb DNA fragments and 10–14 Kb fragments were excised and isolated with the Glass Max DNA Spin Cartridge system (BRL). The HindIII fragments were ligated to the pBluescript KS+ phagemid vector (Stratagene) that had been modified by replacing the ampicillin selectable marker with a neomycin selectable marker (pSTKSN), cleaved with HindIII and dephosphorylated with bacterial alkaline phosphatase. The ligation mixture was used to transform *E.coli* XL1-blue cells (Stratagene) by electroporation at 2.5 Kvolts, 200 ohms, 25 µFd. Transformants were selected on LB agar containing 30 µg/ml neomycin.

3.3 Selection of Clone Containing Hydantoinase Gene

Figure 4:
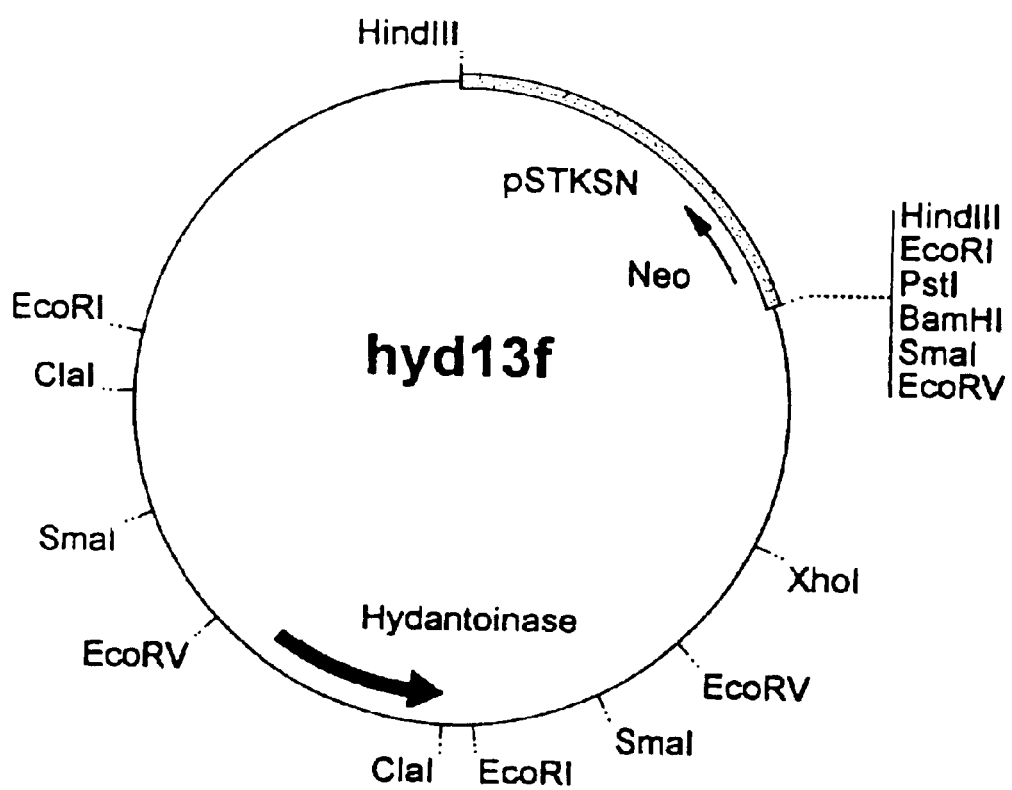
FIG. 4: Schematic representation of plasmid hyd13f.
Figure 5:
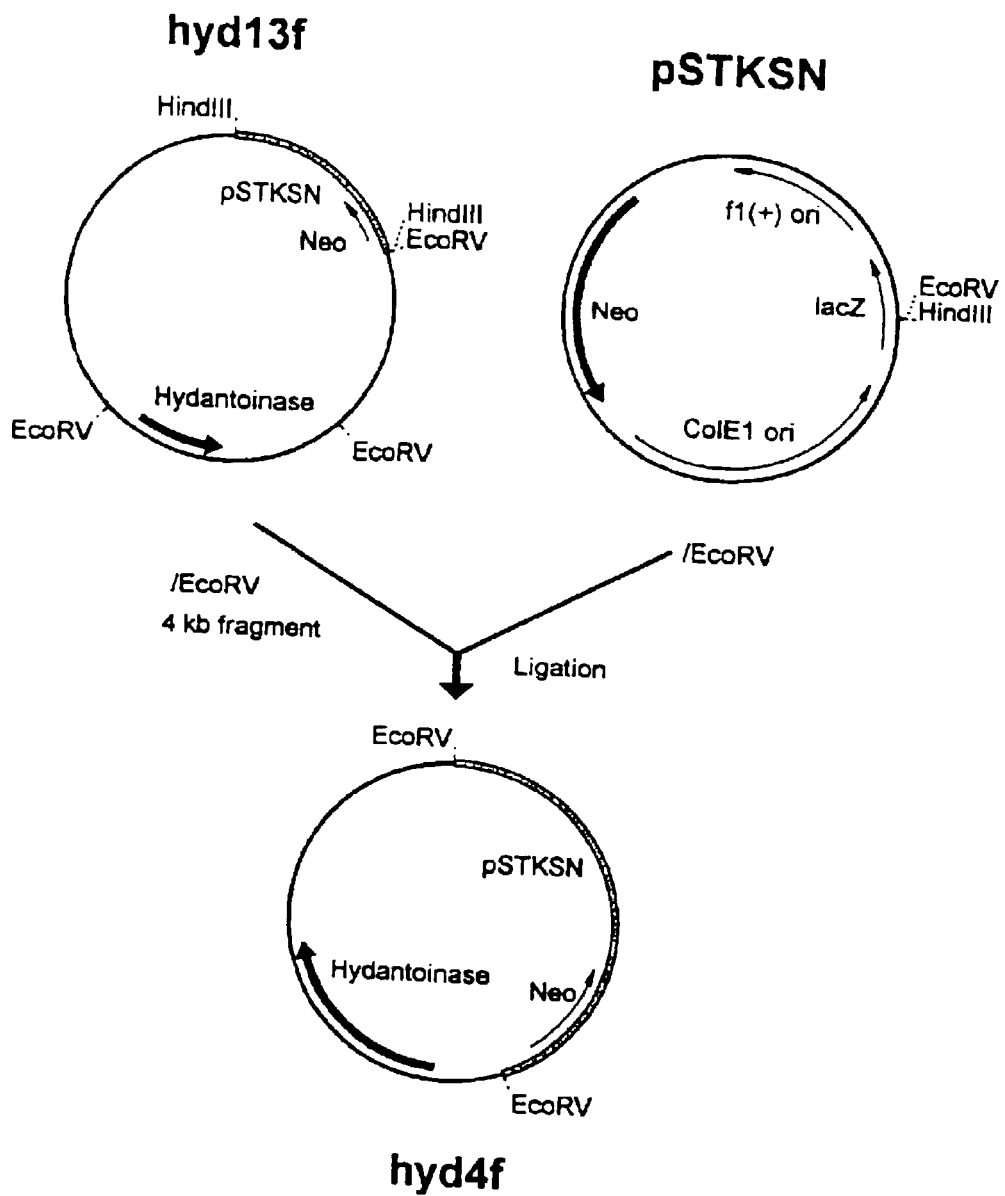
FIG. 5: Schematic representation of plasmid hyd4f.

Colony blots of the genomic library were prepared and screened with the N-terminal oligonucleotide probe. Twelve clones from each fragment were initially selected for further evaluation. Plasmid DNA was isolated from each transformant using the TELT mini-prep method (He, et al., Nucl. Acids Res., 18:1660 (1990)). Southern analysis of these clones identified two that hybridized to the probe. Restriction analysis determined these two clones contained identical 13 Kb HindIII fragments in the same orientation (FIG. 4). Further analysis of the 13 Kb HindIII fragment by primer extension and Southern blotting determined the location and orientation of the hydantoinase gene within the fragment. A 4 Kb EcoRV fragment was isolated from one of the two clones and subcloned into the pBluescript KS+ phagemid vector pSTKSN that had been cleaved with EcoRV and dephosphorylated with bacterial alkaline phosphatase. Plasmid DNA was isolated from 12 colonies as described above and analyzed by EcoRI digestion. Two clones were identified that containd the correct fragment in opposite orientations (FIG. 5). These two clones were assayed for activity and one was shown to produce about twice the amount of. total cellular enzyme as the original Ochrobactrum cells. Nucleotide sequencing of the 4 Kb EcoRV fragment identified the sequence that was complementary to probe 4 (SEQ ID NO:7). Translation of the adjacent DNA sequence produced an amino acid sequence that was identical to the previously determined N-terminal amino acid sequence (SEQ ID NO:3).

3.4 Determination of Nucleotide Sequence

The nucleotide sequence of the hydantoinase gene encoded on the 4 Kb EcoRV fragment was determined by the dideoxy chain termination method (Sanger, et al., Proc. Natl. Acad. Sci., U.S.A. 74:5463–5467 (1977)) using the fmol DNA cycle sequencing system (Promega). The N-terminal oligonucleotide probe used to identify the gene (forward and reverse) and synthesized internal primers were used to sequence the entire gene from both strands. Electrophoresis was performed on a 7% Long Ranger (AT BIOCHEM) polyacrylamide gel containing 7 M urea in TBE (0.089 M Tris-borate, 0.089 M boric acid, 0.002 M EDTA) buffer at 2700 volts. The complete nucleotide sequence is shown in FIG. 6. The coding region is 1440 bp long and codes for a 480 amino acid protein (MW=53 kD). This is consistent with the deglycosylated form of the enzyme (experimental section 1.5 above). The N-terminal protein sequence determined from the translation of the DNA sequence is identical to the protein sequence identified in experimental section 2.5 above.

Example 4

Expression of the Gene for Hydantoinase in *E. coli*.

4.1 Subcloning into Expression Vectors

The coding region of the hydantoinase gene was mutagenized by PCR to insert a BamHI plus NcoI restriction site at the translation start site of the coding region and a BamHI site at the 3' end of the gene to facilitate cloning into the expression vectors. The following primers were synthesized for the PCR reaction:

5'-GGGAACGAGGATCCATGGCAAAGGT-3' (SEQ ID NO:10) (contains BamHI and NcoI sites)

5'-AACTCATGCGCGGATCCCGAAGCTG-3' (SEQ ID NO:11) (contains BamHI site)

Figure 7:
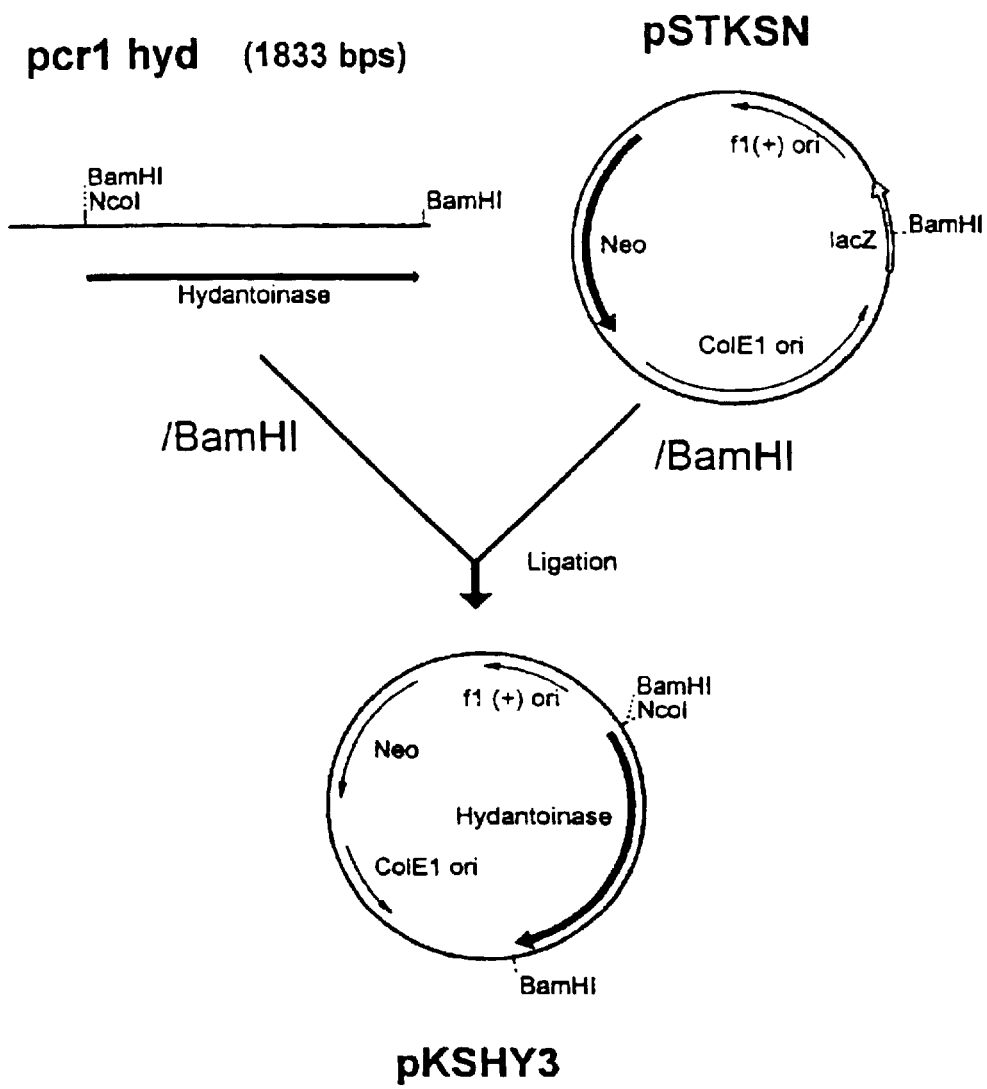
FIG. 7: Construction of pKSHY3
Figure 8:
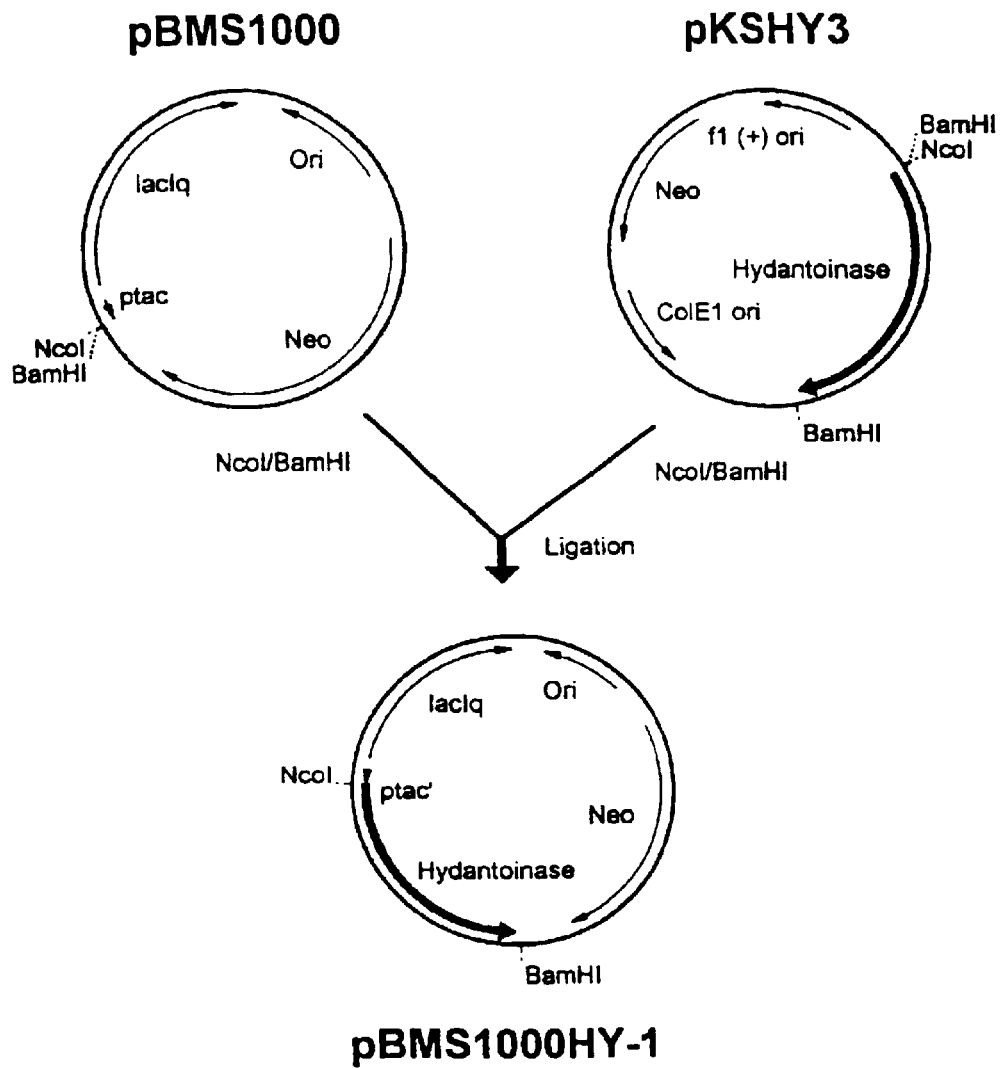
FIG. 8: Construction of pBMS1000HY-1

The PCR fragment was digested with BamHI and column purified with the Glass Max DNA Spin Cartridge system (BRL). This fragment was ligated to the pBluescript phagemid vector pSTKSN that had been cleaved with BamHI and dephosphorylated with bacterial alkaline phosphatase. The ligation mix was used to transform *E.coli* DH5αmcr competent cells (BRL). Plasmid DNA was isolated from 6 colonies as described in experimental section 3.3 above and analyzed by BamHI digestion. Five of the clones contained the correct construct and were further analyzed by NcoI digestion. All five had the NcoI site. One of these was selected for subcloning into several expression vectors (FIG. 7). This clone was named pKSHY3.

pKSHY3 was digested with NcoI and BamHI, then electrophoresed through a 0.8% SeaPlaque (FMC) preparative agarose gel in TAE buffer at 40 volts for 4 hours. The 1479 bp NcoI/BamHI fragment was excised from the gel and isolated with the Glass Max DNA Spin Cartridge system (BRL). This fragment was ligated to expression vector pBMS1000 (U.S. Pat. No. 6,068,991 May 30, 2000, S. W. Lin and T. Franceschini, "High Expression *Escherichia Coli* Expression Vectors", contents of which are herein incorporated by reference) that had been cleaved with NcoI and BamHI. The ligation mix was used to transform *E.coli* DH5αmcr competent cells (BRL). Colonies were screened by NcoI/BamHI digests and all conferred the correct construct (FIG. 8). This clone was named pBMS1000HY-1. This clone was used to transform *E.coli* hosts W3110, BL21, and #7 (ATCC 23736).

4.2 Expression in *E. coli* Hosts

Two clones from each host were selected for shake flask evaluation. Restriction analysis confirmed that each clone contained the correct construct. Fresh overnight cultures were used to inoculate 25 ml T-broth cultures grown under neomycin selection. Cultures were incubated at 37° C. and grown to a $A_{600}$ of 2. A zero time point was measured and then the cultures were induced with 0.4 mM IPTG. One and two hour time points were taken. The cultures were harvested and assayed for activity and time points were analyzed for expression on a 4–20% protein gradient gel (Enprotech), electrophoresed under reducing conditions at 20–25 mA. Protein gels indicate increased levels of expression compared to the original Ochrobactrum cells. Table 7 summarizes the activity results. Based on these results, BL21 was chosen as the best host for further hydantoinase expression studies.

TABLE 7

| Sample | Wet Weight (g/10 ml) | Hydantoinase Activity (IU/g) |
|---|---|---|
| T7-1 | 0.09 | 7.5 |
| W3110-1 | 0.21 | 3.3 |
| W3110-2 | 0.18 | 3.5 |
| BL21-1 | 0.19 | 8.0 |
| BL21-2 | 0.13 | 8.0 |
| 7-1 | 0.16 | 4.6 |
| 7-2 | 0.24 | 4.2 |

Example 5

Characterization and Immobilization of Recombinant Hydantoinase 5.1 Substrate Specificity

*E. coli* BL21 containing the hydantoinase gene was grown as described in example 4.2. The cells were centrifuged and washed with 100 mM carbonate buffer pH 9.0 and resuspended in the same buffer and ruptured by sonication. The enzyme was purified as described in example 2. The purified enzyme was tested for substrate specificity with various hydantoins as substrate. The results are summarized in table 9.

TABLE 9

| Substrate | Specific Activity IU/mg |
|---|---|
| Hydantoin | 7.5 |
| Uracil | 1.8 |
| 2-thio uracil | N.D. |

TABLE 9-continued

| Substrate | Specific Activity IU/mg |
|---|---|
| 5-methyl hydantoin | 10.6 |
| 5,5-diphenyl hydantoin | N.D. |
| Hydroxymethyl 5,5-dimethyl hydantoin | 5.6 |
| p-hydroxymethyl hydantoin | 1.9 |
| D,L hydantoin 5-acetic acid | 1.8 |
| 2-thio hydantoin | 4.3 |

5.2 Metal Ion Requirements

Purified hydantoinase was assayed with hydantoin with the addition of the various metal ions at 100 mM concentration. The results are summarized in table 10 below.

TABLE 10

| Metal Ion Specific activity: | | | |
|---|---|---|---|
| None (EDTA) | 4.8 | Mg (II) | 5.2 |
| Ca (II) | 3.6 | Mn (II) | 7.1 |
| Co (II) | 3.6 | Ni (II) | 3.6 |
| Cu (II) | 1.2 | Zn (II) | 1.8 |
| Fe (III) | 3.8 | | |
| Fe (II) | 9.3 | | |

There is activity in the absence of metal ion but Fe(II) and Mn(II) seem to stimulate the activity of the enzyme.

5.3 Temperature Optimum of Purified and Immobilized Recombinant Hydantoinase

The recombinant enzyme was immobilized as described for the native enzyme in example 1.7. The immobilized enzyme and the purified enzyme were assayed at various temperatures to determine the temperature optima. The results are given in table 11 below.

TABLE 11

| | Relative activity | |
|---|---|---|
| Temperature | Immobilized enzyme | Purified enzyme |
| 25 | 73 | 38 |
| 37 | 100 | 69 |
| 45 | 100 | 100 |
| 55 | 93 | 85 |
| 65 | 94 | 80 |
| 75 | 82 | 66 |

Although the present invention has been described in some detail by way of illustration and example for purposes of clarity and understanding, it will be apparent that certain changes and modifications may be practiced within the scope of the appended claims.

What is claimed is:

1. An isolated nucleic acid molecule comprising a sequence that encodes a polypeptide comprising the amino acid sequence of SEQ ID NO:2.

2. An isolated nucleic acid molecule having a sequence that is complementary to a nucleic acid molecule that encodes SEQ ID NO:2.

3. The nucleic acid molecule of claim 1 which is a DNA molecule.

4. The nucleic acid molecule of claim 2 which is a RNA molecule.

5. An isolated nucleic acid molecule according to claim 1, having the nucleotide sequence of SEQ ID NO:1.

6. An isolated nucleic acid molecule capable of hybridizing under stringent conditions to SEQ ID NO:1.

7. An isolated nucleic acid molecule encoding a polypeptide having an amino acid sequence that is at least 80% homologous to SEQ ID NO:2.

8. An isolated polypeptide having an amino acid sequence that is at least 80% homologous to SEQ ID NO:2.

9. An isolated polypeptide having the amino acid sequence of SEQ ID NO:2.

10. An expression vector comprising a nucleic acid molecule of claim 1.

11. An expression vector comprising a nucleic acid molecule of claim 5.

12. The expression vector of claim 10, further comprising an origin of replication, a promoter, and a transcription termination sequence.

13. The expression vector of claim 12, further comprising a selectable marker gene.

14. The expression vector of claim 10 wherein said vector is a plasmid.

15. The expression vector of claim 14 wherein said plasmid is selected from the group: plasmid hyd13f and plasmid hyd4f.

16. A host cell containing the expression vector of claim 10.

17. A host cell containing the expression vector of claim 12.

18. A host cell containing the expression vector of claim 13.

19. The host cell of claim 16 which is selected from the group: eukaryotic and prokaryotic.

20. A process for producing a polypeptide having the amino acid sequence of SEQ ID NO:2 comprising culturing the host cell of claim 16 under conditions resulting in expression of the polypeptide.

21. A process for stereoselectively converting a 5-monosubstituted hydantoin comprising contacting said 5-monosubstituted hydantoin with the D-hydantoinase as shown in SEQ ID NO:2, or a biologically active fragment or analog thereof, under conditions suitable to form the corresponding D-N-carbamoyl-amino acid.

22. The process of claim 21 wherein said 5-monosubstituted hydantoin is a racemic mixture.

* * * * *